(12) United States Patent
Menne et al.

(10) Patent No.: US 8,865,943 B2
(45) Date of Patent: Oct. 21, 2014

(54) CATALYTIC CONVERSION OF ALCOHOLS AND ALDEHYDES

(75) Inventors: Andreas Menne, Mülheim (DE); Axel Kraft, Oer-Erkenschwick (DE)

(73) Assignee: Fraunhofer-Gesellschaft zur Forderung der Angewandten Forschung, Munich (DE)

( * ) Notice: Subject to any disclaimer, the term of this patent is extended or adjusted under 35 U.S.C. 154(b) by 0 days.

(21) Appl. No.: 13/704,773

(22) PCT Filed: May 5, 2011

(86) PCT No.: PCT/EP2011/002233
§ 371 (c)(1),
(2), (4) Date: Jan. 15, 2013

(87) PCT Pub. No.: WO2011/157322
PCT Pub. Date: Dec. 22, 2011

(65) Prior Publication Data
US 2013/0211146 A1 Aug. 15, 2013

(30) Foreign Application Priority Data
Jun. 17, 2010 (DE) .......................... 10 2010 024 099

(51) Int. Cl.
*C07C 45/29* (2006.01)
*C07C 31/125* (2006.01)
*C07C 29/32* (2006.01)
*C07B 41/06* (2006.01)
*C07B 41/02* (2006.01)
*C07C 15/08* (2006.01)
*C07C 15/067* (2006.01)

(52) U.S. Cl.
CPC ................. *C07B 41/06* (2013.01); *C07C 29/32* (2013.01); *C07C 31/125* (2013.01); *C07C 45/29* (2013.01); *C07B 41/02* (2013.01); *C07C 15/08* (2013.01); *C07C 15/067* (2013.01)
USPC .......................... 568/487; 568/902; 568/902.2

(58) Field of Classification Search
USPC ....................................... 568/487, 902, 902.2
See application file for complete search history.

(56) References Cited

U.S. PATENT DOCUMENTS 4,825,013 A * 4/1989 Quarderer et al. ......... 568/902.2

OTHER PUBLICATIONS

Olson et al. Higher-Alcohol Biorefinery. Improvement of Catalyst for Ethanol Conversion. Applied Biochemistry and Biotechnology, 2004, vol. 113-116, p. 913-932.*

* cited by examiner

*Primary Examiner* — Sikarl Witherspoon (57) ABSTRACT

The invention provides a process for preparing higher alcohols and/or aldehydes and also mixtures thereof by catalytic reaction of ethanol, the reaction taking place in the presence of at least one catalyst, the catalyst comprising an activated-carbon substrate which is provided with at least one metal, and more particularly has at least one metal dope.

15 Claims, 1 Drawing Sheet

CATALYTIC CONVERSION OF ALCOHOLS AND ALDEHYDES

CROSS-REFERENCES TO RELATED APPLICATIONS

This application is a National Stage filing of International Application PCT/EP2011/002233, filed May 5, 2011, claiming priority to German Application No. DE 10 2010 024 099.0 filed Jun. 17, 2010, entitled "CATALYTIC CONVERSION OF ALCOHOLS AND ALDEHYDES." The subject application claims priority to PCT/EP 2011/002233, and to German Application No. DE 10 2010 024 099.0, and incorporates all by reference herein, in their entirety.

BACKGROUND OF THE INVENTION

The present invention relates to the technical field of catalytic reaction or conversion of alcohols and aldehydes, in particular for the preparation of higher alcohols and/or aldehydes or mixtures thereof.

The present invention relates in particular to a process for preparing higher alcohols and/or aldehydes by catalytic reaction of ethanol.

The present invention further relates to the use of an activated carbon substrate provided with at least one metal as catalyst for the catalytic reaction of ethanol.

In addition, the present invention relates to a process for the chain extension of carbon compounds having oxo and/or hydroxy functions by catalytic reaction.

Finally, the present invention relates to the use of an activated carbon substrate provided with at least one metal as catalyst for the catalytic chain extension of carbon compounds having oxo and/or hydroxy functions.

Higher or relatively high molecular weight alcohols and aldehydes and mixtures thereof, in particular $C_3$-$C_{30}$-compounds (i.e. compounds having from 3 to 30 carbon atoms) of the abovementioned type have numerous uses in a variety of industrial fields and are therefore of great industrial importance: thus, higher alcohols and aldehydes are used in industrial processes, for example as solvents, as additives for plastics, paints and varnishes and also as fuels or fuel additives or else as starting materials or building blocks for further syntheses.

For the purposes of the present invention, the terms "higher alcohol" and "higher aldehyde" refer, in particular, to organic compounds having at least one hydroxy and/or aldehyde function and a carbon chain comprising at least three atoms, in particular $C_3$-$C_{30}$-compounds. The carbon chain can be linear or branched and can optionally be interrupted by ether functions.

Furthermore, the higher alcohols and/or aldehydes are generally compounds which are derived from aliphatic hydrocarbons, although part of the hydrogen atoms can be replaced, for example, by functional groups or heteroatoms, for example halogen atoms. However, it is also possible for the higher alcohols and/or aldehydes to be aromatic or partially aromatic systems having at least one hydroxy and/or aldehyde function.

$C_3$-$C_{10}$-alcohols or -aldehydes in particular are of great industrial importance: the primary alcohols of this type are used as solvents or for preparing plasticizers and surfactants and also as additives in varnishes and paints.

In addition, the compounds can also be utilized as starting materials or building blocks for further industrial processes. In this context, 1-butanol is of particular importance and represents a valuable $C_4$ building block whose importance in the future will increase further due to the increasing spread of biosynthetic processes, known as "green processes". Furthermore, 1-butanol can also be used for fuel production or as fuel. 1-Butanol can be added in considerable amounts to commercial spark-ignition fuels, with the use of 1-butanol having the advantage over the use of ethanol that butanol has a higher heating value but is essentially not hygroscopic. In addition, spark-ignition fuel having any proportion of 1-butanol and also pure 1-butanol can be burnt in the spark-ignition engines mass produced at present. For these reasons, the preparation of 1-butanol on the basis of renewable, usually biosynthetic processes is the subject of intensive research at present and 1-butanol from renewable processes is referred to as a third generation biofuel.

However, there have hitherto not been any available processes by means of which selective preparation of 1-butanol from ethanol can be carried out in an economically viable way on an industrial scale.

The corresponding aldehydes are employed as such or optionally after further reaction, in particular hydrogenation, for example as or in solvents, as fuels and fuel additives, as or in plasticizers or in varnishes and paints.

Relatively high molecular weight alcohols are nowadays produced mainly by the oxo process. In this process, propene produced from fossil sources is converted by means of synthesis gas and water into higher alcohols. The reaction requires a high pressure and additionally produces $CO_2$. Increasing costs of fossil raw materials, the high energy consumption and the resulting greenhouse gas emissions make an alternative production method based on renewable raw materials desirable.

In particular, the preparation of higher alcohols and/or aldehydes from $C_1$ and $C_2$ building blocks, for example methanol and ethanol, would be particularly advantageous since these compounds are firstly often obtained as by-products or waste products in "green processes" and secondly can also be produced selectively and in a targeted manner from renewable raw materials.

Thus, for example, lignocellulose can be dissociated into sugars by thermal and/or chemical and subsequent enzymatic treatment and these sugars can be fermented by microorganisms to produce ethanol. In addition, the use of lignocellulose has the advantage that the woody constituents of plants which are not suitable for producing foodstuffs can be made available for further utilization. The utilization of lignocellulose consequently leads not to a competitive use of valuable food and animal feed plants for energy generation or for chemical synthesis; rather, the residues obtained in the growing of foodstuffs, in particular plant constituents which cannot be utilized, can be passed to further beneficial use.

There has therefore been no lack of attempts in the prior art to synthesize these compounds by means of various processes:

One possible way of preparing the higher alcohol butanol on the basis of renewable raw materials is the ABE synthesis. Here, a mixture of acetone, butanol and ethanol is produced by fermentation from biomass. A typical molar ratio of the constituents is 3/6/1. However, butanol is frequently obtained together with by-products of the synthesis and greatly diluted with water in this process. This mixture finally has to be purified with a high process outlay and water has to be separated off with consumption of a great deal of energy. Furthermore, large amounts of $CO_2$ and of methane which is even more damaging to the climate are formed during the fermentation.

Apart from these two known processes, approaches using heterogeneous catalysis in order to produce higher alcohols from the alcohols ethanol or methanol are known. Thus, EP 1 829 851A1 discloses a catalyst based on hydroxyapatite, by means of which butanol, in particular, can be prepared at atmospheric pressure and temperatures up to 400° C. Disadvantages are, in particular, the low selectivity of the conversion into alcohols at relatively high temperatures and the occurrence of aromatic compounds and butadiene and also a low conversion at relatively low temperatures and a low space-time yield. A further disadvantage is the required high dilution of the starting materials or reactants with inert gas.

In addition, a series of further processes which, in particular, are disclosed in the international patent applications WO 2009/026518 A1, WO 2009/026483 A1, WO 2009/026501A1, WO 2009/026506 A1, WO 2009/026523 A1, WO 2009/097310 A1, WO 2009/026510 A1 and WO 2009/097312 A1 and in each case utilize hydrotalcite as catalyst in order to produce higher alcohols from ethanol and from ethanol/methanol mixtures are known. Disadvantages here are the relatively low conversion and the low space-time yield and the required high dilution of the reactants with inert gas, which stand in the way of an economical process.

The scientific publication by Olson et al. "Higher-Alcohols Biorefinery—Improvement of Catalyst for Ethanol Conversion", 2004, Appl. Biochem. Biotechnol. Vol. 113-116, pages 913-932, describes a catalyst based on activated carbon, where activated carbons having BET surface areas in the range from 20 to 100 m$^2$/g and impregnated with alkaline promoters are used as catalysts. However, these activated carbon catalysts are not stable in the synthesis of alcohols or aldehydes from ethanol or methanol and deactivate quickly. Owing to the short life of the catalysts, they cannot be used in industrial processes.

The abovementioned processes of the prior art all have the disadvantage that they produce higher alcohols or aldehydes in only small yields, in particular in low space-time yields, so that these processes are not very efficient and cannot be carried out economically feasibly. In addition, a difficult-to-achieve mode of operation with dilution of the starting materials or reactants with inert gas is necessary in the processes of the prior art. Most of the above-described processes of the prior art use catalyst systems having unsatisfactory operating lives of the catalysts under industrial conditions. It is also often difficult to create controllable reaction conditions so as to obtain reliably reproducible yields and product mixtures. Most of the processes are unsuitable for industrial applications.

BRIEF SUMMARY OF THE INVENTION

It is therefore an object of the present invention to provide a process which is suitable for preparing higher alcohols or aldehydes from low molecular weight starting materials or precursors and at least essentially avoids or at least reduces or decreases the abovementioned disadvantages of the prior art.

To achieve the abovementioned object, the present invention proposes a process as claimed in claim 1; further advantageous embodiments are subject matter of the corresponding dependent claims.

The present invention further provides for the use of an activated carbon substrate as catalyst as described herein.

The present invention additionally provides a process for the chain extension of carbon compounds as taught herein.

Finally, the present invention further provides for the use of a catalyst for the catalytic chain extension of carbon compounds as described herein.

It goes without saying that particular variants and embodiments described below only in connection with one aspect of the invention also apply to the other aspects of the invention without this needing to be explicitly mentioned.

For all relative or percentage amounts, in particular those which are by weight, indicated below, it additionally has to be noted that these are, in the context of the present invention, to be selected by a person skilled in the art in such a way that the sum, if appropriate with inclusion of further components or additives or constituents, in particular as defined below, is always 100%. However, this will be self-evident to a person skilled in the art.

Furthermore, a person skilled in the art can, for the purposes of the application or individual case, deviate from the amounts indicated below without going outside the scope of the present invention.

DETAILED DESCRIPTION OF THE INVENTION

The present invention accordingly provides, according to a first aspect of the present invention, a process for preparing higher alcohols and/or aldehydes and also mixtures thereof by catalytic reaction of ethanol, wherein the reaction is carried out in the presence of at least one catalyst comprising an activated carbon substrate which is provided with at least one metal, in particular doped with at least one metal.

In other words, the catalyst or the activated carbon substrate has, according to the invention, metal doping. As indicated in detail below, the equipping or doping of the catalyst or of the activated carbon substrate can be carried out either during the course of catalyst production or, as an alternative, subsequently; for the purposes of the present invention, it has been found to be advantageous and particularly effective catalysts are obtained when the equipping or doping of the catalyst or the activated carbon substrate is carried out during the course of catalyst production.

The applicant has surprisingly discovered that higher alcohols and/or aldehydes and mixtures thereof can be obtained in a simple and efficient way by a process in which ethanol is reacted in the presence of a catalyst based on an activated carbon substrate provided with a metal. The process of the invention allows, in particular, the selective preparation of higher alcohols or aldehydes in very good yields and can also be carried out economically on an industrial scale. In addition, the process of the invention can be reproduced at will under controlled conditions.

The process of the invention is associated with many advantages, of which at least the important ones will be mentioned below, without being exhaustive:

The process of the invention displays a high selectivity in respect of the formation of alcohols and aldehydes, with, in particular, particularly high selectivities in respect of the formation of $C_3$-$C_6$-alcohols or $C_3$-$C_6$-aldehydes being able to be achieved. When a strongly basic catalyst is used, the formation of butadiene and aromatic compounds can, in particular, be suppressed. The high selectivity of the inventive process allows simple and inexpensive purification, fractionation and subsequent further processing of the product mixture obtained.

Significantly higher space-time yields for alcohols and aldehydes can be obtained by means of the process of the invention compared to processes of the prior art.

The use of a catalyst based on an activated carbon substrate allows, owing to the high specific surface area of the activated carton, a higher alcohol space velocity in the feed stream (expressed in kg of alcohol per kg of catalyst and hour) than hitherto customary. At the same time no or at most only a slight dilution of the reactants with inert gas has to be carried out. This likewise leads to the process of the invention being able to be carried out very economically advantageously or efficiently on an industrial scale.

The production costs for a catalyst based on a metal-laden activated carbon substrate used according to the invention are significantly lower than for conventional transition metal catalysts, in particular when the doping or equipping of the activated carbon substrate is achieved by impregnation of the activated carbon before or after activation of the activated carbon. The doping makes possible a molecular and in particular particularly homogeneous distribution of the active components, as a result of which very high-performance catalysts can be provided with a low usage of metal compounds.

The catalytic surface of the resulting catalyst consists of a combination of the properties of the carbon-containing support material and the specific doping. The catalytic properties can be controlled and/or adjusted in a targeted manner within a wide range by simple variation of the carbon source and doping, which gives a high flexibility in terms of the composition of the product mixture obtained. In particular, the ratio of linear to branched alcohols or aldehydes can be controlled in a targeted way and selectively.

In the process of the invention, basic activated carbon catalysts which are doped with metals or metal compounds and make it possible to achieve a good operating life combined with high activity and high space-time yield are used for the first time. Further advantages are the absence of butadiene formation and the low selectivity to aromatic by-products compared to the prior art.

The process of the invention is conceived as a stand-alone process for preparing higher alcohols and aldehydes. However, it can also be coupled with an oxo process, as a result of which firstly the raw materials costs and catalyst consumption costs can be lowered and secondly a new raw materials basis is opened up in the oxo process. The raw materials costs can, in particular, be lowered since, instead of ever more expensive propylene or relatively long-chain alkenes, cheaper methanol and/or ethanol can be used while still obtaining comparable product mixtures and components. The catalyst consumption costs per mass of alcohol or aldehyde produced are reduced compared to the oxo process since instead of expensive rhodium and cobalt complexes, very much cheaper metal-laden, generally basic activated carbon catalysts can be used.

As indicated at the outset, the terms "higher alcohol" and "higher aldehyde" as used in the context of the present invention refer to organic compounds having the above-defined number of carbon atoms and at least one hydroxy or aldehyde function. These compounds can be either branched or linear or else cyclic carbon chains or frameworks or else be aromatic or partially aromatic systems. For the purposes of the present invention, preference is given to obtaining linear and/or branched chains or frameworks of carbon atoms.

According to the invention, it has been found to be particularly advantageous for the higher alcohols and/or aldehydes to be selected from among linear and branched alcohols and aldehydes.

In general, the higher alcohols and/or aldehydes are, for the purposes of the present invention, selected from the group consisting of $C_3$-$C_{30}$-alcohols and $C_3$-$C_{30}$-aldehydes, in particular $C_3$-$C_{20}$-alcohols and $C_3$-$C_{20}$-aldehydes, preferably $C_3$-$C_{15}$-alcohols and $C_3$-$C_{15}$-aldehydes, and also mixtures thereof.

For the purposes of the present invention, preference is given to obtaining primary alcohols and aldehydes having a chain length of from 3 to 6 carbon atoms, with the $C_3$- and $C_4$-compounds, in particular 1-butanol or n-butanol, being of particular industrial importance. For the purposes of the present invention, it is possible to prepare these short-chain products with particularly high selectivities, and it is at the same time possible to largely suppress the formation of aromatic products.

The product mixture obtained according to the invention can either be separated into individual fractions or into individual compounds which can then be used, for example, as solvents, fuels or fuel additives or starting materials or precursors for the preparation of, for example, plasticizers and additives for varnishes and paints or else plastics.

In addition, it has been found to be particularly advantageous in the context of the present invention for the process of the invention to give a butanol(s)-containing product mixture. The process of the invention can be carried out, in particular, with a particularly high selectivity in respect of the formation of butanol, in particular n-butanol or 1-butanol.

For the purposes of the present invention, ethanol can be reacted as pure material, optionally in the presence of an inert gas, in particular nitrogen. However, it is also possible to react ethanol as a mixture of ethanol with at least one further alcohol, preferably methanol, and/or with at least one aldehyde, optionally in the presence of an inert gas, in particular nitrogen. However, it is also possible, for the purposes of the present invention, for ethanol or the further alcohols and aldehydes optionally present not to have to be used as pure material. That is to say that alcohols and aldehydes can be used as technical-grade compounds, i.e. with a certain proportion of impurities, for the purposes of the present invention. In particular, the alcohols and aldehydes used do not have to have been made absolute; rather, they can have a certain, not inconsiderable proportion of water. Thus, for example, it is possible to use an ethanol/water azeotrope containing 96% by volume of ethanol without further pretreatment or purification for carrying out the process of the invention.

Ethanol is advantageously used in volume-based amounts of from 5 to 100% by volume, in particular from 10 to 100% by volume, preferably from 20 to 100% by volume, particularly preferably from 25 to 100% by volume, based on the starting mixture. If ethanol is not used at a concentration of 100% by volume (i.e. in other words not as pure material), the remaining proportion by volume of the mixture of the starting materials can be formed by inert gas(es), preferably nitrogen, and/or at least one further alcohol, preferably methanol, and/or at least one aldehyde.

In particular, it is possible to carry out the process of the invention using an ethanol/inert gas mixture containing at least 5% by volume of ethanol. Ethanol can equally well be used as pure material, i.e. in a concentration of 100% by volume. This is one of the advantages of the process of the invention since it allows the use of undiluted feed streams, which has hitherto not been able to be achieved by the processes of the prior art.

According to the prior art, an inert gas, usually nitrogen, always has to be added to the ethanol to be reacted, with the volume-based proportion of the inert gas often being greater than the volume-based proportion of ethanol. A carrier gas is frequently used in the processes of the prior art, as a result of which the production costs increase drastically. Firstly, there are the costs for the inert gas and secondly the inert gas has to be heated together with the starting material or materials and cooled again with the products, resulting in additional costs due to energy consumption, which can amount to up to about 20% or even more of the total process costs. In addition, dilution of the starting material or of the feed mixture with an inert or carrier gas significantly reduces the space-time yield of the overall process and consequently reduces the efficiency of the process, with the process costs increasing further at the same time.

In addition, the process of the invention offers the advantage that, compared with the prior art, it can be carried out using starting materials of only technical grade which can be procured inexpensively since they have not been specifically treated or purified.

Furthermore, the selectivity in the formation of the products can also be influenced according to the invention by the targeted selection of the starting materials. Thus, the sole use of ethanol as starting material, optionally in combination with an inert gas, leads to predominantly linear products, i.e. products having unbranched carbon chains; at the same time, a high selectivity of the overall process to the formation of butanol or of $C_4$ products is observed. Products having branched carbon chains, on the other hand, are only obtained at a chain length of more than 4 carbon atoms, with the proportion of these products in the total product mixture being extremely small.

On the other hand, if, for example, ethanol/methanol mixtures are used, preferential formation of $C_3$ and $C_4$ products, in particular propanol and butanols (i.e. isobutanol and n-butanol), is also observed, with the selectivities to the individual products being lower and the proportion of branched products being increased.

Not only the choice of starting materials but also the further process parameters have a great influence on the efficiency and selectivity of the process of the invention and on the yield and the product distribution:

In general, the reaction is carried out in the gas phase in the process of the invention. It has been found to be particularly advantageous for the reaction to be carried out at above the boiling points of the starting materials and/or products, preferably above the boiling points of the starting materials and products.

Particularly good conversions, yields and selectivities are obtained when the reaction is carried out at temperatures in the range from 150° C. to 600° C., in particular from 250 to 450° C., preferably from 300 to 400° C.

Furthermore, the reaction can, according to the present invention, be carried out at reduced pressure, atmospheric pressure or superatmospheric pressure. In this context, it has been found to be advantageous to carry out the reaction at an absolute pressure in the range from atmospheric pressure to 100 bar, in particular in the range from atmospheric pressure to 50 bar, preferably in the range from atmospheric pressure to 25 bar.

The reaction times or contact times also have a great influence on conversions and yields and also on the selectivity of product formation. In general, the reaction is carried out using reaction times and/or contact times in the range from 0.001 to 120 seconds, in particular from 0.01 to 60 seconds, preferably from 0.05 to 30 seconds.

For the purposes of the present invention, the term "contact time" refers, in particular, to the ratio of the volume of the catalyst used to the volume flow of the feed gas or feed gas mixture used.

The conversions, yields and selectivities to be achieved by means of the process of the invention can be matched or optimized in a targeted way to the respective requirements and/or be controlled in a targeted way by variation of the abovementioned parameters. Thus, in particular, the optimum in respect of the conversions, yields and selectivities can be set in a targeted manner by appropriate matching of temperature and pressure, with a temperature increase generally having a positive effect on the conversions and yields, but exceeding a certain temperature range reducing the yields and in particular the selectivity of product formation. An increase in the pressure, on the other hand, generally makes increased conversions, yields and selectivities at lower temperatures possible.

Appropriate setting of the contact times, which determine the residence time of the substances in the reactor and thus the reaction time, enables the conversions, yields and selectivities to be optimized still further. Here, the contact times have to be sufficiently long to ensure good conversions and yields but must not be made excessively long in order to avoid the formation of by-products as far as possible. When the contact times are excessively long, the formation of by-products increases greatly, thus reducing the selectivity of the process.

In general, the formation of alcohols occurs at short contact times and the formation of aldehydes also occurs at longer contact times.

The process of the invention can in principle be operated discontinuously, i.e. batchwise, or else continuously. Preference is given, in particular in the case of technical or industrial use, to a continuous process which makes high space-time yields and conversions possible and can consequently be carried out particularly economically.

In general, the process of the invention is carried out at a space-time yield, reported as amount of all products formed per catalyst volume and per unit time, in the range from 10 to 3000 g/(liter·h), in particular from 25 to 2500 g/(liter·h), preferably from 30 to 2000 g/(liter·h), particularly preferably from 50 to 1500 g/(liter·h).

Here, the process can be carried out with a molar conversion, based on the starting materials used, in particular ethanol, in the range from 20 to 90%, in particular from 30 to 80%, preferably from 40 to 75%.

The molar conversion is, in particular, defined as the ratio of the molar amount of starting material reacted to starting material used, i.e. conversion=(starting material reacted [mol])/(starting material used [mol])·100=(starting material used [mol]−unreacted starting material [mol])/(starting material used [mol])·100.

As indicated above, an increase in the pressure and/or the temperature generally brings about an increase in the conversions, but the increase in the conversion is obtained above a certain point at the expense of the selectivity, so that optimal matching of the individual process parameters has to be determined for each individual case.

The space-time yields and molar conversions indicated above describe ranges in which the process of the invention is particularly economical and can be carried out advantageously from process-economic points of view, with a high selectivity being achieved in the product mixtures obtained.

In this context, the process can also be carried out at a molar selectivity, based on $C_4$ product(s) in particular butanol, and calculated as percentage ratio of the molar amount of $C_4$ product(s) to the molar amount of starting material(s) reacted, in the range from 5 to 70%, in particular from 10 to 60%, preferably from 10 to 50%.

These high selectivities can be achieved without problems using the process of the invention, so that the process of the invention is distinguished further from processes of the prior art. The molar selectivity is here defined, in particular, as ratio of the amount of carbon of the respective product, in particular amount of carbon in $C_4$ products, to the amount of carbon in starting material reacted (selectivity to component i=(amount of carbon in component i in the product mixture [mol])/(amount of carbon in starting material reacted [mol])·100, in particular selectivity to $C_4$ products=(amount of carbon in $C_4$ product [mol])/(amount of carbon in starting material reacted [mol])·100).

Furthermore, the process of the invention can be carried out, in particular, with a molar yield based on $C_4$ product(s), in particular butanol, and calculated as the product of molar conversion and molar selectivity (as defined above) in the range from 5 to 50%, in particular from 5 to 40%, preferably from 5 to 30%.

The molar yield of the component i is, in particular, defined as the product of the molar conversion of the component i and the molar selectivity of the component (yield of component i=conversion (i)·selectivity (i), in particular yield of $C_4$ products=conversion to $C_4$ products·selectivity to $C_4$ products).

The abovementioned molar selectivities and yields are characteristic of the process of the invention and distinguish this from the processes of the prior art.

As indicated above, a catalyst based on a metal-laden activated carbon substrate is used in the process of the invention.

The activated carbon used in the present invention preferably contains not only carbon but also small amounts of oxygen, nitrogen, sulfur and hydrogen, which are chemically bound in the form of various functional groups such as carbonyl, carboxyl, phenol and ether groups and also lactones and quinones. These surface oxides can result from the raw materials or else they can be formed by the activation process, by action of chemical activators and by action of oxygen or water vapor. The chemical properties of the surface play a significant role in adsorption and catalysis.

The starting materials for activated carbon which are suitable for producing catalysts which can be used according to the invention generally have mineral components which can be concentrated during the activation process. Furthermore, it is also possible for inorganic chemicals for the activation of the activated carbon not to be removed completely or to remain in their entirety on the activated carbon.

The ash content of activated carbons is critically determined by the mineral components. The main constituents of this ash are alkali metals and alkaline earth metals, usually in the form of carbonates and phosphates, possibly together with silica and iron oxides and aluminum oxides. The ash content of activated carbons can be reduced by washing with water or acid. Commercial products therefore have ash contents of from less than one percent to twenty percent.

Activated carbon functions simultaneously as catalyst and as catalyst support: the catalytic activity of the activated carbon as such is based essentially on the structure of the carbon skeleton which consists of a mixture of amorphous and graphite-like carbon; at the periphery of layers, there are many chemically unsaturated corners and edges which function as lattice vacancies and the abovementioned surface oxides, which can participate in redox reactions and thus represent the reason for the chemical activity of activated carbons, are preferably present on the internal activated carbon surface of the activated carbons used in the process of the invention. In addition, the activated carbons used according to the invention function as support for the metal doping.

The catalyst used for carrying out the process of the invention and/or the activated carbon substrate used are generally equipped and/or configured so as to be basic.

In particular, the catalyst and/or the activated carbon substrate can have at least one basic functional group and/or at least one basic chemical compound.

Here, it has, in particular, been found to be particularly advantageous for the basic equipping to be provided by (i) hydroxides; (ii) oxides; (iii) salts of inorganic acids, in particular phosphates, sulfates, carbonates and nitrates; (iv) salts of organic acids, in particular lactates, phthalates, formates and acetates; and/or (v) alkoxides.

In a preferred embodiment of the present invention, the basic equipping is provided by carbonates and/or phosphates, particularly preferably by carbonates and phosphates.

The basic equipping can be effected during the production of the catalyst or else subsequently, in particular by means of impregnation. However, particularly good results are obtained in the context of the present invention when the basic equipping is carried out during production of the catalyst.

For the purposes of the present invention, basic equipping means that the catalyst or the activated carbon substrate has basic groups and/or compounds or else groups and compounds which have a basic reaction. It is critical that the basic character of these groups or compounds is retained in the finished catalyst under reaction conditions. It is also quite possible for the compounds originally used to be transformed in the production of the catalyst or else during the catalysis reaction; in this case, the transformation products have to have basic character. Thus, for example, carbonates can react to form oxides during activation of the activated carbon substrate, but it is likewise possible for the carbonates to react with the carbon framework of the activated carbon substrate, for example to form phenoxides, oxides, anhydrides, hydroxides, etc.

In addition, the catalyst used according to the invention should have a large specific surface area. The catalyst used in the process of the invention and/or the activated carbon substrate generally has a specific surface area (BET) in the range from 450 to 3000 m$^2$/g, in particular from 500 to 2500 m$^2$/g, preferably from 600 to 2250 m$^2$/g, particularly preferably from 900 to 1700 m$^2$/g, very particularly preferably from 950 to 1500 m$^2$/g, even more preferably from 1000 to 1350 m$^2$/g.

In addition, the catalyst used according to the invention should have a large micropore volume. In particular, the catalyst and/or the activated carbon substrate can have a micropore volume, in particular a micropore volume determined by the Gurvich method, in the range from 0.1 to 3.0 ml/g, in particular from 0.2 to 2.5 ml/g, preferably from 0.25 to 1 ml/g, particularly preferably from 0.3 to 0.7 ml/g.

Furthermore, it has been found to be advantageous for the purposes of the present invention for the catalyst and/or the activated carbon substrate to have an operating life of at least 10 days, in particular at least 20 days, preferably at least 30 days, particularly preferably at least 6 months. Long operating lives of the catalyst used according to the invention make it possible for the process of the invention to be carried out continuously in industry and thus make an economically advantageous preparation of higher alcohols and aldehydes possible.

It has likewise been found to be advantageous for the catalyst and/or the activated carbon substrate to comprise at least one functional group, preferably a polar and/or ionic functional group. The at least one functional group can be selected from among carbonyl, carboxylate, hydroxyl, oxide, ether, ester, lactone, phenol and quinone groups. The abovementioned functional groups can, for example, be formed by reactions of the carbon framework of the activated carbon substrate with a compound required for the basic equipping during the activation of the activated carbon substrate (as described above).

In general, the metal, in particular the metal doping, of the catalyst used in the process of the invention is selected from the group consisting of alkali metals, alkaline earth metals, metals of the transition groups of the Periodic Table of the Elements and the rare earths and also mixtures or combinations thereof.

Furthermore, the catalyst can have at least one monovalent metal $M^I$, in particular at least one alkali metal, preferably sodium and/or potassium, and/or at least one divalent metal $M^{II}$, in particular calcium and/or magnesium, particularly preferably at least one monovalent metal $M^I$ and at least one divalent metal $M^{II}$.

The catalyst can likewise contain phosphorus, in particular in the form of phosphates.

Particularly good results are obtained in the process of the invention when the abovementioned compounds and/or substances are present in specific molar ratios relative to one another in the catalyst used according to the invention. In this context, preference is given, for the purposes of the present invention, to the catalyst having the following molar ratios:
(i) $0.5 \leq M^I/M^{II} \leq 5$, in particular $2 \leq M^I/M^{II} \leq 3$; and/or
(ii) $2 \leq M^{II}/P \leq 30$, in particular $2 \leq M^{II}/P \leq 8$; and/or
(iii) $1 \leq M^I/P \leq 60$, in particular $5 \leq M^I/P \leq 10$; and/or
(iv) $1 \leq K/Na \leq 20$, in particular $10 \leq K/Na \leq 20$; and/or
(v) $1 \leq Ca/Mg \leq 10$, in particular $4 \leq Ca/Mg \leq 6$.

Very good results are likewise obtained in the process of the invention when the catalyst comprises the following proportions (percent by weight) of the following components, where the following amounts are in each case based on the catalyst:
(i) $M^I$, in particular sodium and/or potassium, preferably sodium and potassium: from 0.1 to 20% by weight, in particular from 0.2 to 15% by weight, preferably from 0.5 to 10% by weight; and/or
(ii) $M^{II}$, in particular calcium and/or magnesium, preferably calcium and magnesium: from 0.1 to 20% by weight, in particular from 0.2 to 10% by weight, preferably from 0.5 to 5% by weight; and/or
(iii) P, in particular in the form of phosphate, calculated as phosphorus P: from 0.01 to 5% by weight, in particular from 0.02 to 2.5% by weight, preferably from 0.02 to 1% by weight.

Particularly good conversions, yields and selectivities can be achieved in the process of the invention when the catalyst used according to the invention contains the abovementioned metals and phosphorus both in the specific molar ratios relative to one another and also in the respective absolute molar proportions.

In particular, an activated carbon which has been equipped so as to be basic and/or be made basic and is provided with at least one alkali metal and/or alkaline earth metal doping, preferably alkali metal and alkaline earth metal doping, particularly preferably potassium and calcium and/or magnesium doping, can be used as catalyst for the purposes of the present invention. Here, it has been found to be particularly advantageous to use a potassium- and calcium- and/or magnesium-doped activated carbon which has been made basic by means of phosphate and/or carbonate.

In a particular embodiment of the present invention, a shaped activated carbon as is disclosed in DE 10 2004 033 561A1 and DE 10 2004 033 561 B4, whose total relevant disclosure content is hereby fully incorporated by reference, can be used as catalyst.

In this embodiment, the catalyst used is a shaped activated carbon which can be produced by a process for producing shaped activated carbon from a carbon carrier, a binder and a catalytic component of the general formula (I)

$$[M]_{m3}[AO_{n4}]_{m4} \qquad (I)$$

where
M is a cation and is selected from the group consisting of alkali metal and alkaline earth metal cations;
m3 and m4 are stoichiometric coefficients which are integers, where $m3 \geq 1$ and $m4 \geq 1$;
$[AO_{n4}]$ is an oxygen-containing anion having the integral stoichiometric coefficient $n4 \geq 1$;
$[AO_{n4}]$ is preferably selected from the group consisting of carbonates and hydroxides;
where the binder is obtained from the reaction of a water-soluble carbohydrate-containing starting material having a glucose content of ≥50% by weight, in particular ≥60% by weight, the carbon carrier is firstly mixed with the catalytic component, the mixture of catalytic component and carbon carrier is subsequently mixed with the binder, the resulting mixture of carbon carrier, catalytic components and binder is pressed to form shaped bodies and the shaped bodies are carbonized and activated, where the binder is obtained from the reaction of the carbohydrate-containing starting material with an additive and the additive is added to the carbohydrate-containing starting material before mixing of the binder with the mixture of the carbon carrier and the catalytic component in order to give the binder; here, the additive can, in particular, be selected from the group consisting of phosphoric acids and salts thereof, sulfuric acids and salts thereof and sulfuric acid derivatives and salts thereof.

This general production process and the chemical composition of the compounds of the metals, transition metals and rare earths in the doping are originally aimed at the adsorption of acidic gases. To produce a particularly effective catalyst which can be used in the process of the invention, this production process can be adapted slightly, with the adaptions being fully disclosed in DE 10 2004 033 561A1 and DE 10 2004 033 561 B4.

As doping reagent for the alcohol synthesis, use is made in the case of the shaped activated carbon for the alcohol or aldehyde synthesis of metal salts whose cations are selected from among the metals of main groups 1 and 2, the transition metals, the rare earths and the semi-metals.

$K_2CO_3$ is preferably added as activator to the carbon carrier. Potassium carbonate reacts with the carbon carrier with, inter alia, consumption of carbon and leads to the formation of very small micropores which are widened further during the gas activation by means of steam to give larger micropores and mesopores and thus lead to the desired pore system. Variation of the amount of $K_2CO_3$ in the carbon carrier and the activation conditions (temperature, amount of steam, residence time, etc.) therefore allows different pore sizes and pore distributions to be set in the shaped activated carbon.

The envisaged additives, for instance $K_2CO_3$, have to be added to the carbohydrate-containing starting material for the binder before mixing of the binder with the carbon carrier. The binder for the production of shaped activated carbon can be obtained from the reaction of a water-based glucose-containing starting material with an additive selected from the group consisting of phosphoric acids and salts thereof. The water-based glucose-containing starting material is preferably glucose or a glucose derivative, preferably glucose syrup, thickened juice or fruit syrup. These sugar-containing starting materials have a low ash content of <5% by weight, in particular <2% by weight, which is likewise advantageous for the properties of the shaped activated carbon. In principle, it is possible to use all carbohydrates, for example monosaccharides (in particular glucose, fructose, mannose, galactose, etc.) and/or disaccharides (in particular sucrose, maltose, lactose, cellobiose, trehalose, etc.) and/or trisaccharides, tetrasaccharides, oligosaccharides and polysaccharides (in particular starch, cellulose, glycogen, etc.) and/or predissolved starch or cellulose, in particular in the form of aqueous solutions, as starting materials. Mixtures of various sugars can also be used.

If phosphoric acid is selected as additive for the conversion of the water-based glucose-containing starting material into a binder, it is preferable and advantageous for the binder which can be obtained after mixing of the phosphoric acid with the water-based glucose-containing starting material not to be neutralized. If this binder is subsequently mixed with a carbon carrier to produce shaped activated carbon, neutralization of the acidic groups of the binder by basic groups of the carbon carrier occurs. Omission of the process step of neutralization significantly simplifies the outlay in the production of the binder. In addition, it is also possible and likewise advantageous to use a salt of phosphoric acid directly as additive to the water-based glucose-containing starting material in the production of the binder.

In this embodiment, preference is given to the additive having the general formula (II)

$$[M_{m1}][H_{n1}P_{n2}O_{n3}]_{m1} \qquad (II)$$

where

M is a proton (H$^+$) or a cation selected from the group consisting of alkali metal, alkaline earth metal, ammonium, calcium, magnesium and iron ions, preferably from among alkali metal, alkaline earth metal and ammonium ions, where H is hydrogen and P and O are phosphorus and oxygen, respectively, m1 and m2 are stoichiometric coefficients and are integers where m1≥1 and m2≥1;

[H$_{n1}$P$_{n2}$O$_{n3}$] is an anion having integral stoichiometric coefficients n1, n2 and n3 where n1>0, n2>1, n3>2.

Phosphoric acid (H$_3$PO$_4$) is particularly suitable as additive for the carbohydrate-containing or sugar-containing binder.

In the presence of phosphoric acids, the carbohydrate-containing starting material is dehydrated to form carbon. This process is illustrated for the example of glucose in the following equation:

$$C_{12}H_{22}O_{11} \rightarrow 12C + 11H_2O$$

This forms a carbon modification which, compared to the added carbon carrier (e.g. wood charcoal, carbonized fruit kernels, etc.), is attacked only slowly by water vapor.

In general, it is possible to use carbonates, nitrates, sulfates or other organic salts which form oxides at high temperatures above 400° C., but preferably at activation temperatures of from 500 to 950° C., as precursors for forming the surface oxides.

The additive can also be selected from among (tri)ammonium phosphate, (di)ammonium hydrogenphosphate, ammonium dihydrogenphosphate, (tri)potassium phosphate, (di)potassium hydrogenphosphate, potassium dihydrogenphosphate and mixtures thereof:

(Di)ammonium hydrogenphosphate is particularly suitable as additive because of the high water solubility in a water-based glucose-containing starting material. In the reaction of the additive with the water-based carbohydrate-containing or glucose-containing starting material, (di)ammonium hydrogenphosphate, for example, reacts catalytically with the sugar of the binder, with the sugar being aromatized in a number of reaction steps. The catalytic effect is due, in particular, to phosphates becoming attached to or condensing with the OH group of the sugar with elimination of water and subsequently being eliminated to form a double bond in the sugar ring, ultimately with aromatization or olefin formation.

If the activated carbon is activated by means of steam, the aromatized binder reacts significantly less readily with steam than the carbon carrier during activation of the shaped activated carbon. The aromatization process of the sugar proceeds essentially catalytically, with the ash content of the activated carbon not increasing or increasing only insignificantly.

The carbon carrier is preferably carbon from renewable raw materials, in particular wood charcoal or other lignocellulose-based natural materials. However, it is in principle also possible to mix fossil carbon carriers, in particular brown coal and/or brown coal coke and/or hard coal and/or mixtures of renewable and fossil carbon carriers, with the binder for producing shaped activated carbon. Furthermore, it is also possible to use synthetic polymers, for example ones based on polyvinylbenzene or the like, including heteroatom-containing synthetic polymers, as carbon carriers.

The shaped activated carbon used in this embodiment contains the catalytically active components or dopants homogeneously distributed in a carbon-containing matrix. Owing to the high temperatures which prevail during the production process, it may be assumed that the dopants are partially and/or completely chemically changed. For example, the dissociation pressure of potassium carbonate according to the following equilibrium at 1000° C. is about 5 torr:

$$K_2CO_3 \leftrightarrow K_2O + CO_2$$

Furthermore, it is known that potassium carbonate forms surface complexes containing C—O—K fragments with the carbon carrier. Likewise, the formation of intercalation compounds in which, in particular, metallic potassium is located on lattice sites between the sheets of a graphite lattice structure is postulated in the specialist literature. X-ray structure analyses of activated carbons show that carbon is encountered not only in amorphous form but also in the form of very small crystals which have the normal graphite lattice structure.

It can therefore be assumed, without wishing to be tied to this theory, that the shaped activated carbons no longer have the dopants originally used in the active sites formed from the dopants but instead at least partly have units, in particular clusters and intercalation compounds, having a different chemical structure. It may be assumed that the intercalation compounds are restricted only to the graphite lattice structure.

It is also known that intercalation compounds are formed with alkali metals and alkaline earth metals which act as very strong reducing agents and at the same time actively participate in hydrogen storage and hydrogen transfer reactions.

For further details in this respect of the catalyst in this embodiment, reference may be made to DE 10 2004 033 561 A1 and DE 10 2004 033 561 B4.

In a further, alternative particular embodiment of the present invention, a shaped activated carbon as is described in DE 10 2006 025 450 A1 or in WO 2007/137856 A2 belonging to the same patent family, whose total disclosure content is hereby fully incorporated by reference, can be used as catalyst.

In this embodiment, the catalyst used is a shaped activated carbon which can be produced from a pressable composition which contains a milled carbon-containing material, a binder and at least one metal-containing doping reagent and is pressed, dried, carbonized and subsequently activated by means of an activating gas, where a first doping reagent which is a metal salt whose metal is selected from the group of metals of main groups 3 to 6 of the Periodic Table of the Elements, transition metals, rare earths and semi-metals and/or is an iodide of the alkali metals or alkaline earth metals is present and a second doping reagent of the formula M$^2_p$(EO$_q$)

r, where $M^2$ is selected from among alkali metals and alkaline earth metals, E is an element of main groups 3 to 7 of the Periodic Table of the Elements and p, q and r are each integers ≥1, is optionally present; here, the second doping reagent can, in particular, be selected from among hydroxides and carbonates.

The present invention further provides, according to a second aspect of the present invention, for the use of an activated carbon substrate provided with at least one metal as catalyst for the catalytic reaction of ethanol to form higher alcohols and/or aldehydes and admixtures thereof, in particular $C_3$-$C_{30}$-alcohols and/or $C_3$-$C_H$-aldehydes and mixtures thereof.

As regards further details of this aspect of the invention, reference may be made to what has been said above regarding the first aspect of the invention, which also applies analogously to this aspect of the invention.

The present invention also provides, according to a third aspect of the present invention, a process for the chain extension of carbon compounds having at least one oxo and/or hydroxy function by catalytic reaction in the presence of at least one catalyst, where the catalyst comprises an activated carbon substrate provided with at least one metal.

The process of the invention can consequently be used not only for the preparation of higher alcohols or aldehydes from ethanol-containing feed mixtures; rather, the process of the invention can also be used generally for the chain extension of carbon compounds having oxo and/or hydroxy functions. Primary and secondary alcohols and aldehydes and ketones are particularly suitable for this type of process; it merely has to be ensured that at least one starting component has at least one hydrogen atom on a carbon atom in the alpha position or vicinal position relative to the functional group. This means that methanol and formaldehyde or mixtures thereof are not suitable as sole starting component.

Apart from this exception, many carbon compounds having oxo and hydroxy functions, in particular primary and secondary alcohols and also aldehydes and ketones, can be reacted using the process of the invention. In particular, compounds having more than three or four carbon atoms can also be used as starting materials and be converted into products having an even greater chain length. This process of chain extension is, however, limited by the condition that both products and starting materials should not condense in the reactor, i.e., in particular, formation of a liquid phase in the reactor should not occur since otherwise the catalyst could be damaged.

For further details regarding this aspect of the invention, reference may be made to what has been said above with regard to the other aspects of the invention, which applies analogously.

Finally, the present invention further provides, according to a fourth aspect of the present invention, for the use of a catalyst comprising an activated carbon substrate provided with at least one metal as catalyst for the catalytic chain extension of carbon compounds having at least one oxo and/or hydroxy function.

For further details regarding this aspect of the invention, reference may be made to what has been said above with regard to the further aspects of the invention, which applies analogously to this use according to the invention.

Further embodiments, modifications and variations and also advantages of the present invention can be readily recognized and achieved by a person skilled in the art on reading the description, without going beyond the scope of the present invention.

The present invention is illustrated by the following examples which do not, however, restrict the present invention.

EXAMPLES

Example 1

Atmospheric Pressure System

Figure 1:
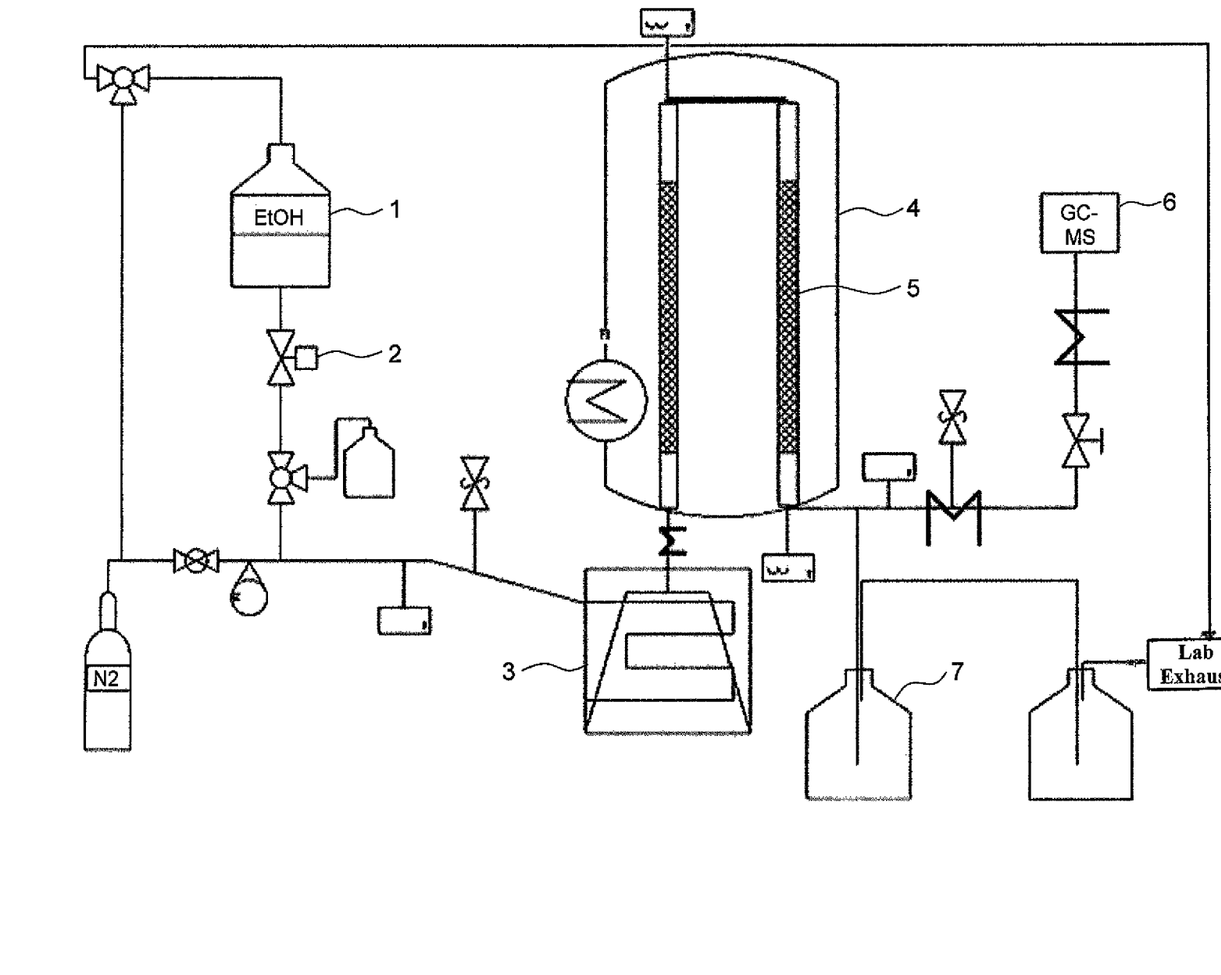
FIG. 1 provides a schematic depiction of the experimental set-up utilized in the examples.

Pellets produced according to the invention from shaped activated carbon are comminuted mechanically and the fragments (1-2 mm fraction) are introduced into a stainless steel reactor. The reactor has an internal diameter of 9 mm and a length of 135 mm. The mass of catalyst introduced is 10 g or 45 g. A schematic depiction of the experimental set-up used is shown in the one FIGURE.

Both pure ethanol and aqueous ethanol are possible as starting material or reactant. Mixtures of various alcohols and aldehydes are likewise possible.

The reactants are located in a pressure vessel 1 and are metered via a calibrated mass flow regulator 2. Before entry into the vaporizer, inert gas, generally nitrogen, can optionally be added. The volume flow is set by means of a needle valve with a floating body flowmeter and is typically in the range from 0 to 40 l of $N_2$/h. The reactants are vaporized and heated to up to 380° C. in an electrically heated tube 3. The inert gas is likewise heated to up to 380° C. The gaseous mixture flows from the vaporizer into the reactor 4 in which the reaction proceeds at the surface of the catalyst 5. The temperatures in the reactor are in the range from 350 to 425° C. Typical contact times are in the range from 0.01 to 30 seconds. After passing through the reactor, the product mixture is condensed in one or more cold traps 7 and the proportion which cannot be condensed at room temperature is discharged in gaseous form. Direct sampling of the product gas stream is possible via a heated line.

The composition of the liquid products is determined by means of HPLC (HPLC 1200 with RI detector and a Rezex ROA, 300×7.8 mm column of Phenomenex from Agilent) and the water content of the sample is determined by Karl-Fischer titration. Further products are determined by means of GC/MS (GC/MS+FID 6890N/5975 with a DB-FFAP, 30 m×0.25 mm×0.25 µm column from Agilent).

Selected experimental results are shown in the tables presented (experiments 1 to 4, 8 and 14 to 17). Apart from the compounds indicated there, mainly water from the reaction is present in the product. Furthermore, depending on the process conditions, xylene and alkylbenzenes and also ethyloctanol and dodecanol are present in the product.

Apart from the liquid phase, the composition of the gaseous products formed is also determined (the analytical results are not explicitly listed). The analyses show that hydrogen, ethane and carbon dioxide form main components (in mol %) here. Further components are traces of alkanes and alkenes having a variety of chain lengths. However, only a very small proportion of gaseous products (<5% by weight) is formed overall, especially at temperatures below 380° C. However, with increasing temperature or residence time, the proportion can rise to up to 20% by weight.

Apart from the study on the reaction of pure or aqueous ethanol, mixtures of alcohols or aldehydes can also be reacted by the process. An experiment using a methanol/ethanol feed mixture is shown by way of example as experiment 7 in table 2. Compared to the use of pure ethanol, the proportion of branched compounds and also the proportion of compounds having an odd number of carbon atoms increase significantly when using a methanol/ethanol mixture.

Example 2

System Under Superatmospheric Pressure

To carry out experiments under superatmospheric pressure, too, a second plant in which the ethanol is conveyed by means of an HPLC pump from a reservoir into a vaporizer heated to 300° C. by means of oil was utilized. The reaction proceeds over 45 g of the catalyst described in a reactor which has a volume of 120 ml and is heated electrically to the reaction temperature. The product is condensed in two water-cooled heat exchangers after the reaction. Experiments are carried out at a pressure of up to 21 bar (absolute) using this plant. The mass flow of ethanol is in the range from 45 to 90 g/h. The results are shown as experiments 5 and 6 and also 9 to 13 in the tables.

An increase in pressure leads first and foremost to a significant reduction in the concentration of aldehydes in the product. The proportion of higher alcohols likewise increases significantly compared to the process under atmospheric pressure, even at low temperatures.

Catalyst Systems Used

In the above examples, alkali metal- and alkaline earth metal-doped activated carbon substrates made basic by means of phosphate, as are obtained in accordance with DE 10 2004 033 561 A1, are used as catalysts. The catalyst systems "Cat1", "Cat2" and "Cat3" used are chemically characterized in more detail below:

Chemical Composition of the Catalysts Used, Based on Ash:

Cat1:

| | |
|---|---|
| Ash content | 24.4% by weight |
| Sodium | 7.28 g/kg |
| Potassium | 238 g/kg |
| Magnesium | 11.7 g/kg |
| Phosphorus | 19.2 g/kg |
| Calcium | 167 g/kg |
| Total | 443.18 g/kg |

Cat2:

| | |
|---|---|
| Ash content | 18.1% by weight |
| Sodium | 10.7 g/kg |
| Potassium | 360 g/kg |
| Magnesium | 13.9 g/kg |
| Phosphorus | 36.5 g/kg |
| Calcium | 110 g/kg |
| Total | 531.1 g/kg |

Cat3:

| | |
|---|---|
| Ash content | 11.0% by weight |
| Sodium | 22.2 g/kg |
| Potassium | 307 g/kg |
| Magnesium | 11.8 g/kg |
| Phosphorus | 5.6 g/kg |
| Calcium | 130 g/kg |
| Total | 476.6 g/kg |

Molar Chemical Composition of the Catalysts Tested:

| | Na | K | Mg | Ca | P | | | | |
|---|---|---|---|---|---|---|---|---|---|
| Cat1 | 0.3 | 6.1 | 0.5 | 4.2 | 0.6 | 0.5 Na/P | 9.8 K/P | 0.8 Mg/P | 6.7 Ca/P |
| Cat2 | 0.5 | 9.2 | 0.6 | 2.7 | 1.2 | 0.4 Na/P | 7.8 K/P | 0.5 Mg/P | 2.3 Ca/P |
| Cat3 | 1.0 | 7.9 | 0.5 | 3.2 | 0.2 | 5.3 Na/P | 43.5 K/P | 2.7 Mg/P | 18.0 Ca/P |

TABLE 1

Product compositions from experiments using ethanol as starting material under various reaction conditions; 10 g (atmospheric pressure system; 1 bar) or 45 g of catalyst (system under superatmospheric pressure) were used

| No. | Ethanol [g/l] | Butanol [g/l] | Hexanol [g/l] | Octanol [g/l] | Ethanal [g/l] | Butanal [g/l] | Hexanal [g/l] | Alcohols, total [g/l] | Aldehydes, total [g/l] | T [° C.] | m [g/h] | $N_2$ [l/h] | p [bar] |
|---|---|---|---|---|---|---|---|---|---|---|---|---|---|
| 1 | 495 | 68 | 8.1 | 1.4 | 39.8 | 11.5 | 2.4 | 78 | 53.7 | 405 | 20 | 1 | 1 |
| 2 | 626 | 55.9 | 6.8 | 0 | 14 | 4 | 0 | 63 | 18.0 | 385 | 15 | 25 | 1 |
| 3 | 281 | 72.0 | 13.6 | 1.4 | 27.7 | 20.0 | 8.7 | 87 | 56.4 | 425 | 5 | 4 | 1 |
| 4 | 549 | 77.7 | 13.7 | 3 | 11.5 | 11.5 | 3.7 | 94 | 26.7 | 350 | 2 | 4 | 1 |
| 5 | 512 | 80.5 | 19.9 | 5.6 | 8.0 | 1 | 0 | 106 | 9.0 | 360 | 60 | 0 | 11 |
| 6 | 482 | 91.3 | 23.8 | 6.3 | 5.9 | 6.3 | 1.3 | 121 | 13.4 | 380.0 | 60.0 | 0 | 21 |

TABLE 2

Product composition for an experiment using a methanol/ethanol mixture (5:1) as starting material under atmospheric pressure (1 bar) and 10 g of catalyst

| No. | Methanol [g/l] | Ethanol [g/l] | Propanol [g/l] | Isobutanol [g/l] | Butanol [g/l] | Hexanol [g/l] | Octanol [g/l] | Ethanal [g/l] |
|---|---|---|---|---|---|---|---|---|
| 7 | 344 | 141 | 82 | 51 | 17.9 | 1.1 | 0 | 7.4 |

| Butanal [g/l] | Hexanal [g/l] | Alcohols, total [g/l] | Aldehydes, total [g/l] | T [° C.] | m [g/h] | N [l/h] |
|---|---|---|---|---|---|---|
| 0 | 0.0 | 152.2 | 7.4 | 400 | 8 | 30 |

TABLE 3

Experimental conditions and molar conversions for further experiments (No. 8 to 17) using ethanol as a starting compound

| No. | Temperature [° C.] | Pressure [bar] | Mass flow of starting material [g/h] | Mass of catalyst [g] | Catalyst volume [l] | Volume flow of nitrogen [l/h] | Space-time yield [g/(h · l)] | Conversion [%] |
|---|---|---|---|---|---|---|---|---|
| 8  | 360 | 1  | 11.4 | 45 | 0.1   | 0  | 74  | 65 |
| 9  | 380 | 21 | 90   | 45 | 0.1   | 0  | 398 | 44 |
| 10 | 380 | 21 | 45   | 45 | 0.1   | 0  | 279 | 62 |
| 11 | 380 | 21 | 60   | 45 | 0.1   | 0  | 371 | 62 |
| 12 | 380 | 11 | 90   | 45 | 0.1   | 0  | 465 | 52 |
| 13 | 360 | 11 | 60   | 45 | 0.1   | 0  | 337 | 56 |
| 14 | 405 | 1  | 20   | 10 | 0.015 | 1  | 695 | 52 |
| 15 | 385 | 1  | 15   | 10 | 0.015 | 25 | 447 | 45 |
| 16 | 425 | 1  | 5    | 10 | 0.015 | 4  | 276 | 83 |
| 17 | 350 | 1  | 2    | 10 | 0.015 | 4  | 55  | 41 |

TABLE 4

Product distribution and molar selectivities [%] for experiments 8 to 17 using ethanol as starting compound

| No. | Acetaldehyde | Butanal | Hexanal | Octanal | Butanol | Hexanol | Octanol | Xylene | Ethylbutanol | Alkylbenzene | Ethylhexanol | Decanol | Total |
|---|---|---|---|---|---|---|---|---|---|---|---|---|---|
| 8  | 4.9 | 4.9 | 1.7 | 0.4 | 28.9 | 7.3 | 1.8 | 1.4  | 3.0  | 0.7  | 1.7  | 0.7  | 57.4 |
| 9  | 3.2 | 0.0 | 0.0 | 0.0 | 25.7 | 4.3 | 0.7 | n.d. | n.d. | n.d. | n.d. | n.d. | 33.8 |
| 10 | 1.0 | 1.2 | 0.2 | 0.0 | 18.5 | 5.2 | 1.5 | 1.4  | 2.5  | 0.7  | 1.5  | 0.7  | 34.6 |
| 11 | 1.7 | 0.0 | 0.3 | 0.0 | 22.6 | 5.1 | 1.1 | 2.1  | 2.8  | 0.9  | 1.3  | 0.5  | 38.3 |
| 12 | 3.4 | 0.0 | 0.0 | 0.0 | 15.5 | 2.2 | 0.0 | n.d. | n.d. | n.d. | n.d. | n.d. | 21.0 |
| 13 | 1.8 | 2.1 | 0.6 | 0.0 | 26.1 | 7.9 | 2.4 | 1.2  | 3.1  | 0.7  | 2.0  | 1.3  | 49.1 |
| 14 | 7.7 | 2.7 | 0.6 | 0.4 | 15.7 | 2.0 | 0.4 | n.d. | n.d. | n.d. | n.d. | n.d. | 29.5 |
| 15 | 2.9 | 1.0 | 0.0 | 0.4 | 13.8 | 1.8 | 0.0 | n.d. | n.d. | n.d. | n.d. | n.d. | 19.9 |
| 16 | 2.2 | 2.0 | 0.9 | 0.0 | 6.9  | 1.4 | 0.2 | n.d. | n.d. | n.d. | n.d. | n.d. | 13.6 |
| 17 | 6.0 | 0.8 | 0.0 | 0.0 | 20.9 | 2.6 | 0.5 | n.d. | n.d. | n.d. | n.d. | n.d. | 30.8 | n.d. = not determined

TABLE 5

Molar yields [%] from experiments 8 to 17 using ethanol as starting compound

| No. | Acetaldehyde | Butanal | Hexanal | Octanal | Butanol | Hexanol | Octanol | Xylene | Ethylbutanol | Alkylbenzene | Ethylhexanol | Decanol | Total |
|---|---|---|---|---|---|---|---|---|---|---|---|---|---|
| 8  | 3.2 | 3.2 | 1.1 | 0.2 | 18.8 | 4.7 | 1.2 | 0.9  | 2.0  | 0.4  | 1.1  | 0.5  | 37.4 |
| 9  | 1.4 | 0.0 | 0.0 | 0.0 | 11.4 | 1.9 | 0.3 | n.d. | n.d. | n.d. | n.d. | n.d. | 15.0 |
| 10 | 0.6 | 0.8 | 0.1 | 0.0 | 11.5 | 3.3 | 0.9 | 0.9  | 1.6  | 0.5  | 0.9  | 0.5  | 21.5 |
| 11 | 1.0 | 0.0 | 0.2 | 0.0 | 14.0 | 3.2 | 0.7 | 1.3  | 1.7  | 0.5  | 0.8  | 0.3  | 23.7 |
| 12 | 1.8 | 0.0 | 0.0 | 0.0 | 8.0  | 1.1 | 0.0 | n.d. | n.d. | n.d. | n.d. | n.d. | 10.9 |
| 13 | 1.0 | 1.2 | 0.3 | 0.0 | 14.6 | 4.5 | 1.3 | 0.7  | 1.7  | 0.4  | 1.1  | 0.7  | 27.5 |
| 14 | 4.0 | 1.4 | 0.3 | 0.2 | 8.2  | 1.1 | 0.2 | n.d. | n.d. | n.d. | n.d. | n.d. | 15.4 |
| 15 | 1.3 | 0.5 | 0.0 | 0.2 | 6.1  | 0.8 | 0.0 | n.d. | n.d. | n.d. | n.d. | n.d. | 8.9  |
| 16 | 1.8 | 1.6 | 0.8 | 0.0 | 5.7  | 1.2 | 0.1 | n.d. | n.d. | n.d. | n.d. | n.d. | 11.2 |
| 17 | 2.5 | 0.3 | 0.0 | 0.0 | 8.7  | 1.1 | 0.2 | n.d. | n.d. | n.d. | n.d. | n.d. | 12.8 | n.d. = not determined

The invention claimed is:

1. A process for preparing higher alcohols and aldehydes and mixtures thereof by catalytic reaction of ethanol,
   wherein the reaction is carried out in the presence of at least one catalyst comprising an activated carbon substrate which is provided with at least one metal,
   wherein the catalyst has at least one monovalent metal $M^I$ in the form of an alkali metal and at least one divalent metal $M^{II}$ in the form calcium and/or magnesium, and wherein the catalyst contains phosphorus in the form of phosphates,
   wherein the following molar ratios apply:
   (i) $0.5 \leq M^I/M^{II} \leq 5$;
   (ii) $2 \leq M^{II}/P \leq 30$; and
   (iii) $1 \leq M^I/P \leq 60$.

2. The process as claimed in claim 1, wherein the higher alcohols and aldehydes are selected from the group consisting of $C_3$-$C_{30}$-alcohols and $C_3$-$C_{30}$-aldehydes and mixtures thereof.

3. The process as claimed in claim 1, wherein the higher alcohols and aldehydes are selected among linear and branched alcohols and aldehydes and wherein a butanol-containing product mixture results.

4. The process as claimed in claim 1, wherein ethanol is reacted as pure material or else as a mixture of ethanol with at least one further alcohol or with at least one aldehyde.

5. The process as claimed in claim 1, wherein the reaction is carried out in the gas phase and wherein the reaction is carried out at above the boiling points of the starting materials and products.

6. The process as claimed in claim 1, wherein the reaction is carried at temperatures in the range from 150° C. to 600° C.

7. The process as claimed in claim 1, wherein the reaction is carried out using reaction times or contact times in the range from 0.001 to 120 seconds.

8. The process as claimed in claim 1, wherein the process is carried out with a space-time yield, calculated as amount of all products formed per catalyst volume and per unit time, in the range from 10 to 3000 g/(liter·h).

9. The process as claimed in claim 1, wherein the process is carried out with a molar conversion, based on the starting materials used, in the range from 20 to 90%.

10. The process as claimed in claim 1, wherein the process is carried out at a molar selectivity, based on $C_4$ products and calculated as percentage ratio of the molar amount of $C_4$ products to the molar amount of starting materials reacted, in the range from 5 to 70%.

11. The process as claimed in claim 1, wherein the process is carried out with a molar yield based on $C_4$ products and calculated as the product of molar conversion and molar selectivity in the range from 5 to 50%.

12. The process as claimed in claim 1, wherein the activated carbon substrate has a specific surface area (BET) in the range from 450 to 3000 m$^2$/g and a micropore volume determined by the Gurvich method in the range from 0.1 to 3.0 ml/g.

13. The process as claimed in claim 1, wherein the activated carbon substrate has an operating life of at least 10 days.

14. The process as claimed in claim 1, wherein the activated carbon substrate comprises at least one functional group selected from among carbonyl, carboxylate, hydroxyl, oxide, ether, ester, lactone, phenol and quinone groups.

15. A process for the chain extension of carbon compounds having at least one oxo or hydroxy function by catalytic reaction in the presence of at least one catalyst,
wherein the catalyst is an activated carbon substrate provided with at least one metal
wherein the catalyst has at least one monovalent metal $M^I$ in the form of an alkali metal and at least one divalent metal $M^{II}$ in the form calcium and/or magnesium, and wherein the catalyst contains phosphorus in the form of phosphates,
wherein the following molar ratios apply:
(i) $0.5 \leq M^I/M^{II} \leq 5$;
(ii) $2 \leq M^{II}/P \leq 30$; and
(iii) $1 \leq M^I/P \leq 60$.

* * * * *